(12) United States Patent
Hotoda et al.

(10) Patent No.: US 8,039,617 B2
(45) Date of Patent: Oct. 18, 2011

(54) METHOD FOR PRODUCING ALPHA FORM CRYSTALS OF SAPROPTERIN HYDROCHLORIDE

(75) Inventors: Katsumi Hotoda, Edogawa-ku (JP); Hiroomi Kiyono, Funabashi (JP); Shinnosuke Tazawa, Chiba (JP)

(73) Assignees: Shiratori Pharmaceutical Co., Ltd., Narashino-shi (JP); Daiichi Sankyo Company, Limited, Tokyo (JP)

( * ) Notice: Subject to any disclaimer, the term of this patent is extended or adjusted under 35 U.S.C. 154(b) by 706 days.

(21) Appl. No.: 11/910,498

(22) PCT Filed: Apr. 13, 2006

(86) PCT No.: PCT/JP2006/308264
§ 371 (c)(1),
(2), (4) Date: Oct. 2, 2007

(87) PCT Pub. No.: WO2006/112495
PCT Pub. Date: Oct. 26, 2006

(65) Prior Publication Data
US 2009/0270619 A1   Oct. 29, 2009

(30) Foreign Application Priority Data
Apr. 14, 2005   (JP) .................................. 2005-116687

(51) Int. Cl.
*C07D 475/04* (2006.01)
*A61P 25/00* (2006.01)
(52) U.S. Cl. ...................................................... 544/257
(58) Field of Classification Search .................... 544/257
See application file for complete search history.

(56) References Cited

U.S. PATENT DOCUMENTS

| | | | |
|---|---|---|---|
| 4,595,752 A | 6/1986 | Azuma et al. | |
| 4,713,454 A | 12/1987 | Sakai et al. | |

FOREIGN PATENT DOCUMENTS

| | | | |
|---|---|---|---|
| JP | 60-178887 | | 9/1985 |
| JP | 09 157270 | | 6/1997 |
| WO | WO 2005065018 | * | 7/2005 |

OTHER PUBLICATIONS

Schircks, et al., "A New Regiospecific Synthesis of L-Biopterin [2])", Helvetica Chimica Acta, vol. 68, No. 6, pp. 1639-1643, XP009063871, 1985.

Schircks, et al., "Herstellung von (6 R, S)-5,6,7,8-Tetrahydro-L-biopterin, 7,8-Dihydro-L-biopterin, L-Sepiapterin, Deoxysepiapterin, (6 R, S)-5,6-Dihydrodeoxysepiapterin und 2'-Deoxybiopterin[1])", Helvetica Chimica Acta, vol. 61, No. 7, pp. 2731-2738, XP-002391645, 1978.

* cited by examiner

*Primary Examiner* — James O Wilson
*Assistant Examiner* — Cecilia M Jaisle
(74) *Attorney, Agent, or Firm* — Oblon, Spivak, McClelland, Maier & Neustadt, L.L.P.

(57) ABSTRACT

A method for selectively producing stable alpha form crystals of sapropterin hydrochloride is provided. In this method, the alpha form crystal of sapropterin hydrochloride is produced by dissolving sapropterin hydrochloride with hydrochloric acid at a concentration of not less than 4 mol/L at not less than 70 degrees C.; adding heated ethanol to the solution; and cooling the solution at a cooling rate of not faster than 3 degrees C./min to a temperature of 40 to 55 degrees C. to precipitate the crystals.

4 Claims, 6 Drawing Sheets

METHOD FOR PRODUCING ALPHA FORM CRYSTALS OF SAPROPTERIN HYDROCHLORIDE

TECHNICAL FIELD

This invention relates to a method for selectively producing α form crystals of sapropterin hydrochloride which has excellent storage stability and thermal stability.

BACKGROUND TECHNOLOGY

Sapropterin hydrochloride (L-tetrahydrobiopterin dihydrochloride) is a drug used in treating hyperphenylalaninemia. Hyperphenylalaninemia is a disease caused by a defect in a gene which exhibits symptoms including central nervous symptoms such as mental retardation, melanin deficient symptoms, and abnormal urine odor, all of which are caused by abnormal phenylalanine metabolism.

Sapropterin hydrochloride is produced by using 1',1'-diethylsulfonyl-L-rhamnose for the starting material to produce L-biopterin, and reducing this L-biopterin (see non-patent documents 1 and 2 and patent documents 1 to 5). In these documents, sapropterin hydrochloride is isolated as crystals, and these documents are utterly silent about stability of the crystals.

[Non-patent document 1] Helv. Chim. Acta, 68(6), 1639-1643 (1985)

[Non-patent document 2] Helv. Chim. Acta, 61, 2731 (1978)

[Patent document 1] Japanese Patent Publication No. 2-12475

[Patent document 2] Japanese Patent Publication No. 4-13357

[Patent document 3] Japanese Patent Publication No. 5-86393

[Patent document 4] Japanese Patent No. 2711828

[Patent document 5] Japanese Patent Application Laid-Open No. 9-157270

The crystals of sapropterin hydrochloride produced by the methods as described above were problematic in terms of thermal stability and hygroscopicity, and there has been a demand for development of a method which enables stable supply of highly stable crystals.

SUMMARY OF THE INVENTION

In view of the situation as described above, an object of the present invention is to provide a method for producing crystals of sapropterin hydrochloride which has excellent heat and moisture stability in a stable manner.

The inventors of the present invention produced crystals of the sapropterin hydrochloride under various conditions and evaluated the crystals for their stability, and in the course of such evaluation, found that sapropterin hydrochloride has crystallographic polymorphism. More specifically, the inventors found that sapropterin hydrochloride has two types of crystals, namely, α form and β form, and the crystals having the inferior thermal and moisture stability that had been known were β form. Further investigation revealed that α form crystals having the superior thermal and moisture stability can be produced at a high efficiency in a stable manner by adjusting precipitation temperature, cooling rate and concentration of hydrochloric acid in the recrystallization or crystallization.

Accordingly, the present invention provides a method for producing α form crystal of sapropterin hydrochloride comprising the steps of dissolving sapropterin hydrochloride with hydrochloric acid at a concentration of not less than 4 mol/L at not less than 70° C.; adding heated ethanol to the solution; and cooling the solution at a cooling rate of not faster than 3° C./min to a temperature of 40 to 55° C. to precipitate the crystals.

The present invention is capable of producing α form crystals of the sapropterin hydrochloride having excellent thermal and moisture stability at a high efficiency in a stable (i.e., reproducible) manner. Accordingly, a sapropterin hydrochloride which is useful as a medical starting material can be supplied in stable manner.

PREFERRED EMBODIMENTS OF THE INVENTION

Figure 1:
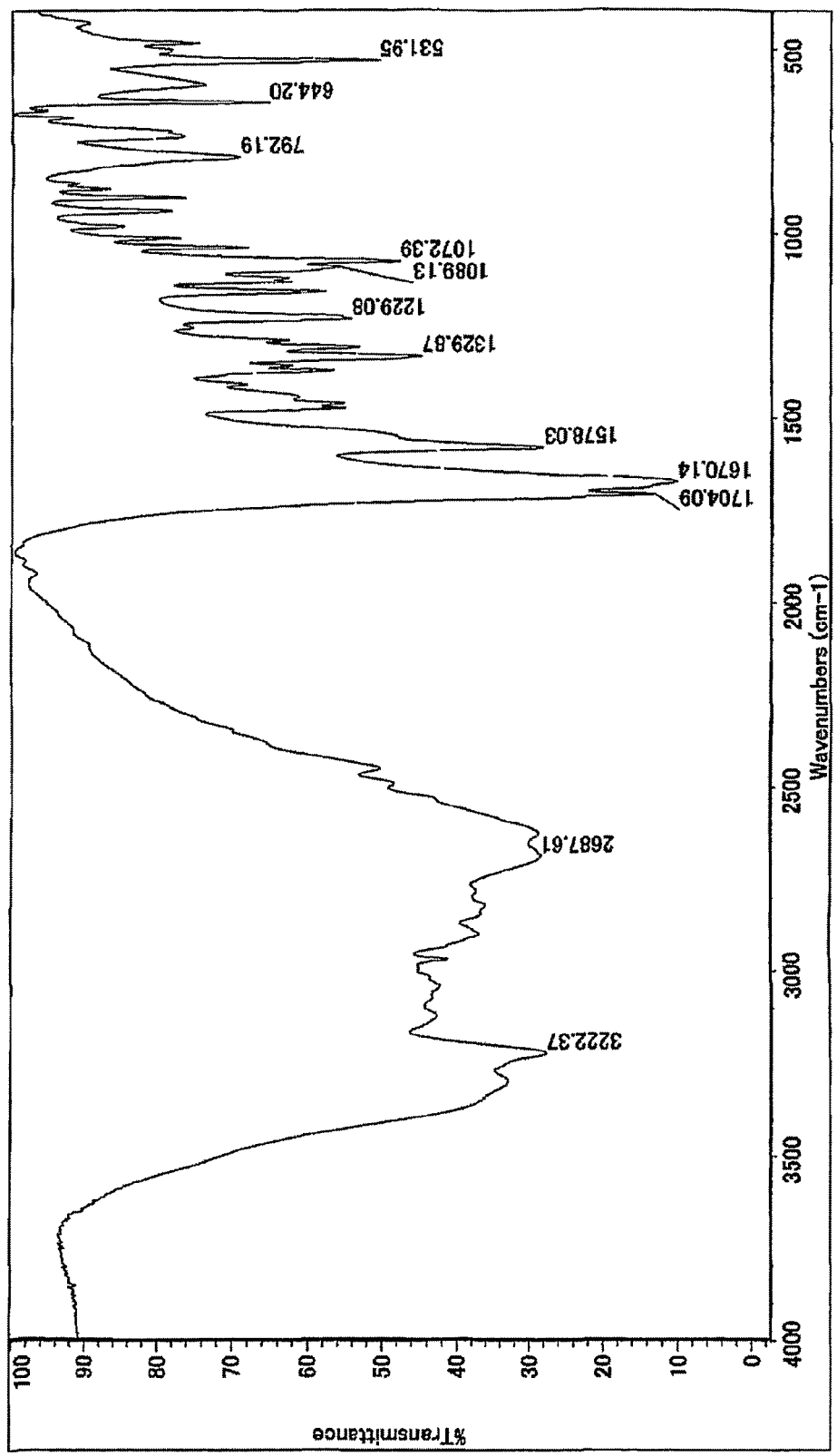
FIG. 1 is a view showing infrared absorption spectrum of α form crystal.
Figure 2:
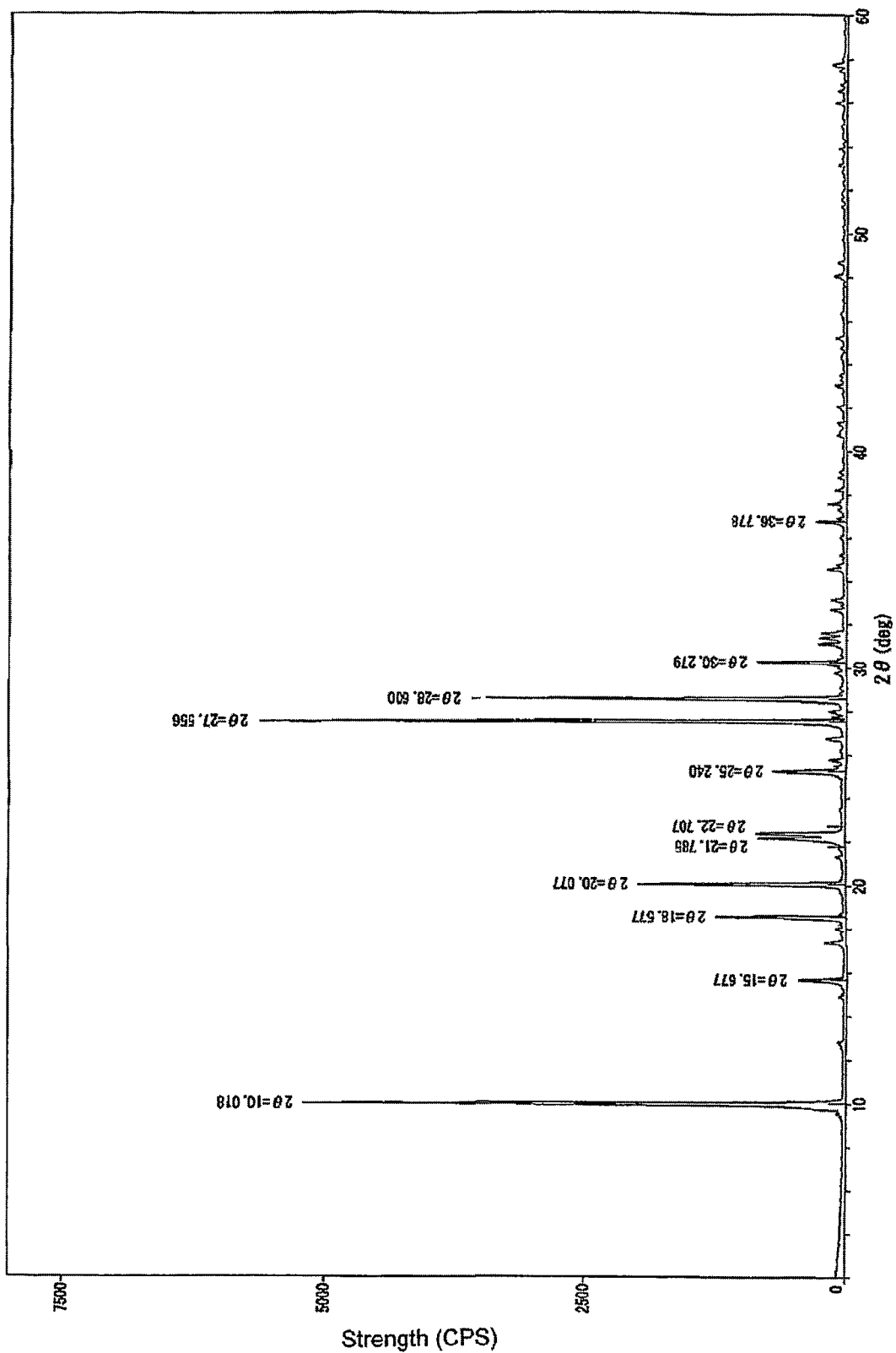
FIG. 2 is a view showing X ray diffraction spectrum of α form crystal.

The sapropterin hydrochloride used in the method of the present invention may be β form crystal, a mixture of α form and β form, or a powder thereof, and the target of the present invention is α form crystal. The α form crystal has infrared absorption spectrum as shown in FIG. 1 and X ray diffraction spectrum as shown in FIG. 2. In other words, this α form crystal has peaks in the infrared absorption spectrum at 1578 $cm^{-1}$, 1089 $cm^{-1}$, and 1072 $cm^{-1}$, 792 $cm^{-1}$, and peaks in the X ray diffraction spectrum at 2θ=10.0°, 20.0°, and 27.5°.

Figure 3:
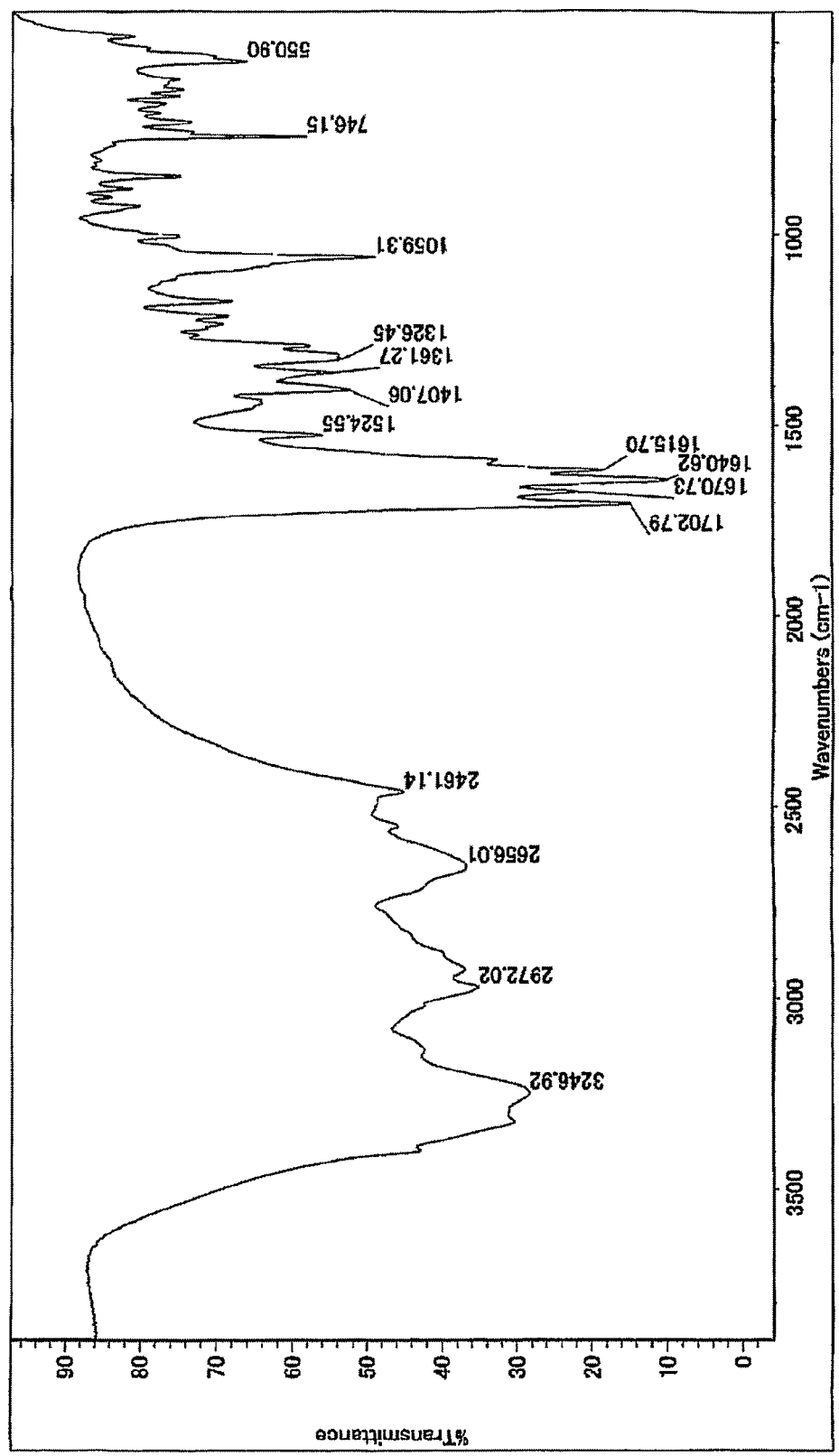
FIG. 3 is a view showing infrared absorption spectrum of β form crystal.
Figure 4:
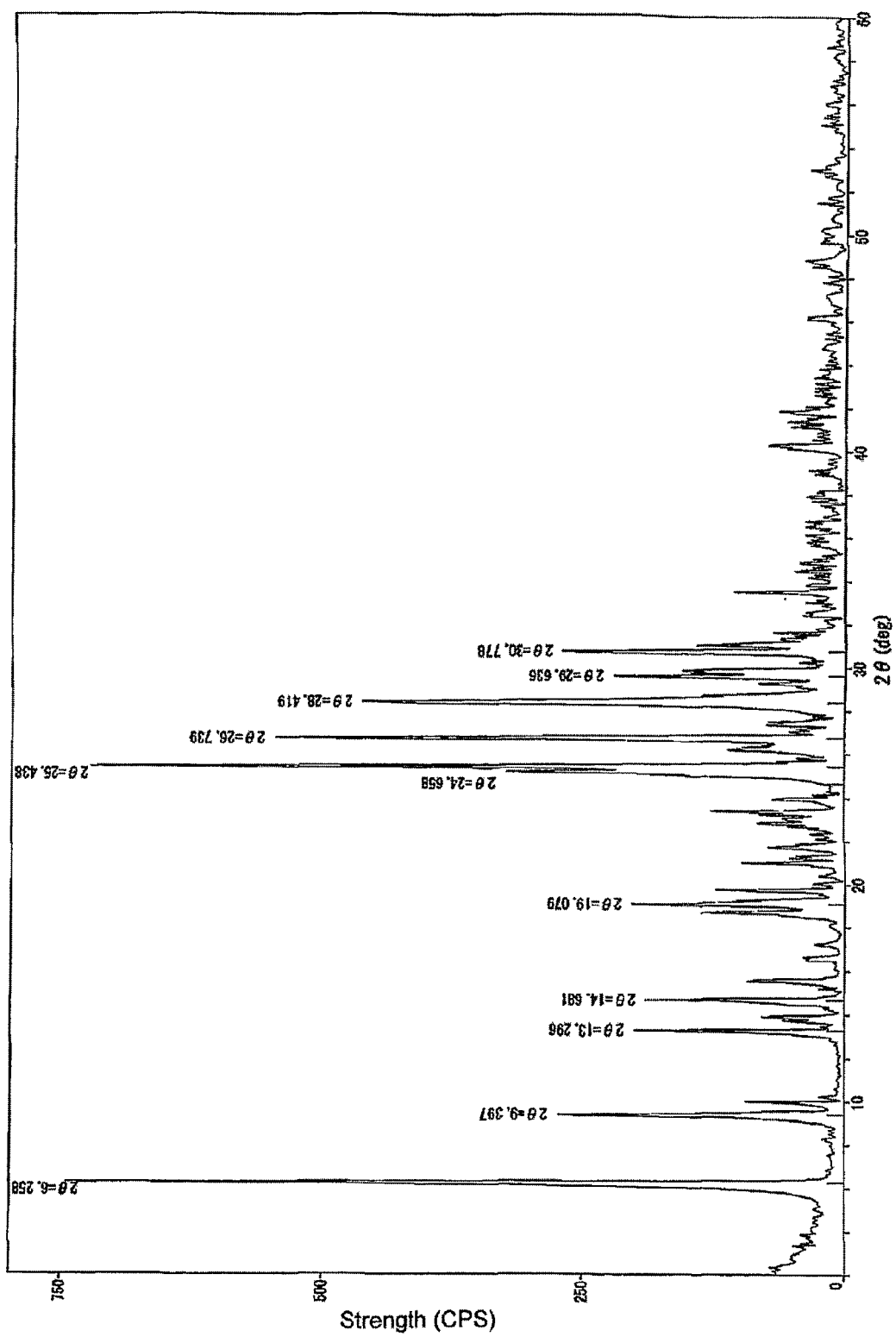
FIG. 4 is a view showing X ray diffraction spectrum of β form crystal.

On the other hand, the β form crystal has infrared absorption spectrum as shown in FIG. 3 and X ray diffraction spectrum as shown in FIG. 4. In other words, the β form crystal has absorption at 1640 $cm^{-1}$, 1615 $cm^{-1}$, 1329 $cm^{-1}$, 1059 $cm^{-1}$, and 746 $cm^{-1}$, and peaks in the X ray diffraction spectrum at 2θ=6.2°, 9.4°, 25.4°, 26.7°, 28.4°, and 30.8°.

With regard to moisture absorption, α form crystal undergoes increase in weight by moisture absorption of 0.85 to 2% during storage for 14 days under the conditions of 25° C. and at relative humidity of 20 to 75%. Increase in weight, however, is stable from day 1 to day 14. On the other hand, weight of the β form crystal gradually increases under the conditions of 25° C. and a relative humidity of 60%, and weight increase is 3.5% at 18 hours and the increase continues to the maximum of 3.9%. From this, α form crystal is more moisture-stable than β form. Furthermore, in contrast to the β form crystal which changes the color from white to pale yellow due to moisture absorption, α form crystal does not change its color by the moisture absorption. Accordingly, α form crystal is suitable for storage.

Figure 5:
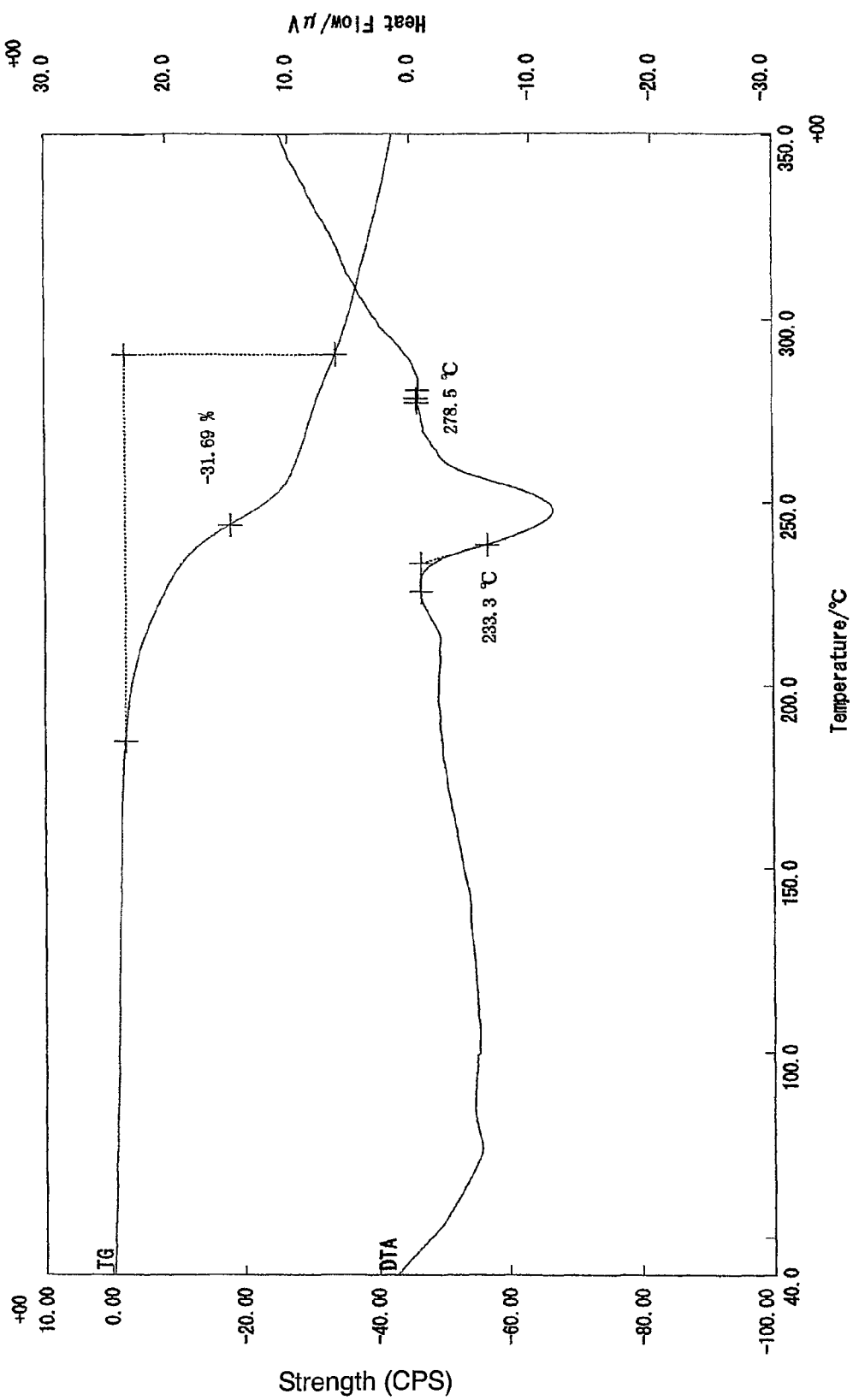
FIG. 5 is a view showing the results of differential thermal analysis for α form crystal.
Figure 6:
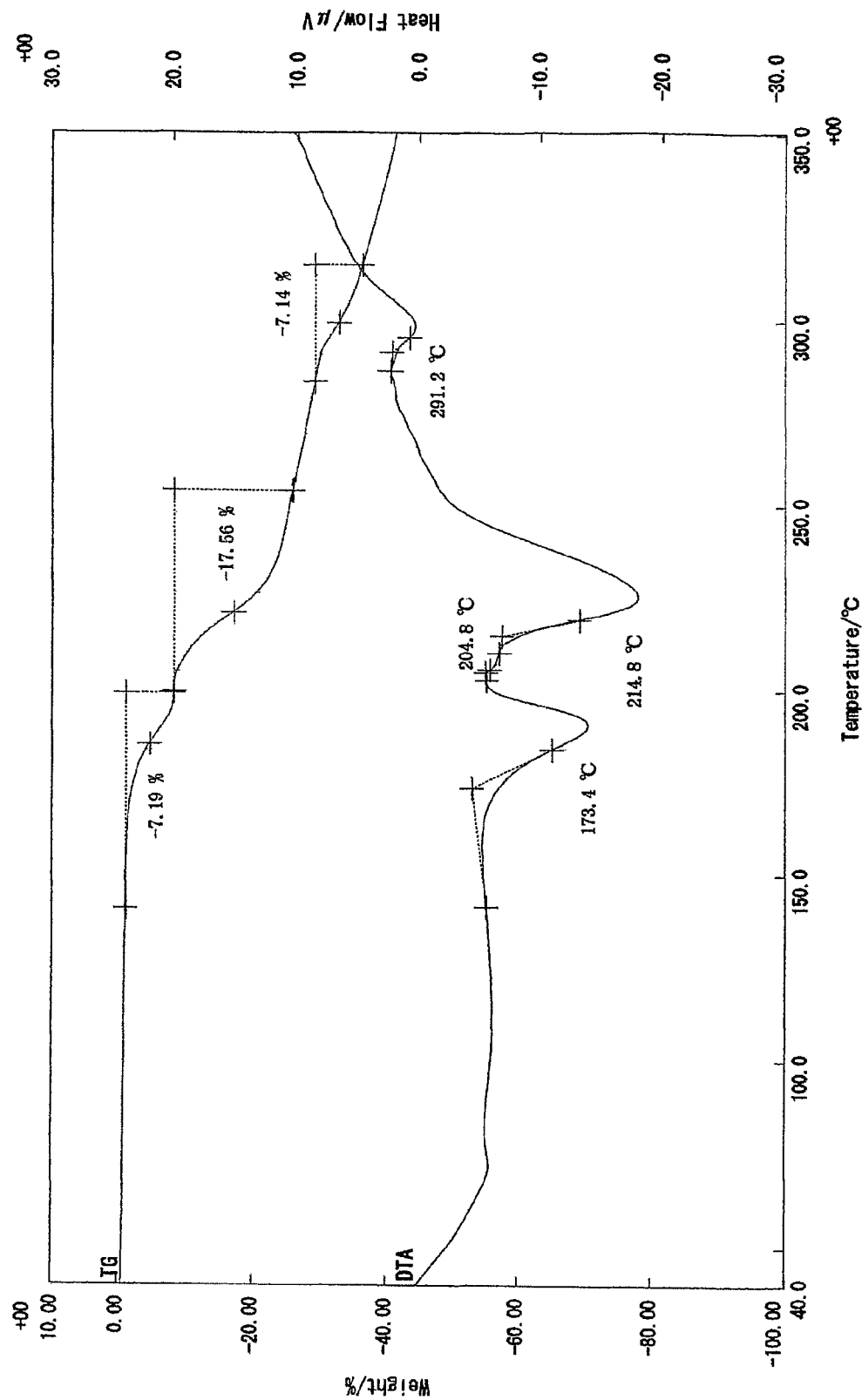
FIG. 6 is a view showing the results of differential thermal analysis for β form crystal.

Furthermore, in differential thermal analysis, α form crystal has only one endothermic peak near the 250° C. as shown in FIG. 5 while β form crystal has two endothermic peaks near 180° C. and near 230° C. as shown in FIG. 6. Accordingly, α form crystal is superior in thermal stability compared to the β form crystal.

In the present invention, sapropterin hydrochloride is dissolved by using hydrochloric acid at a concentration of not less than 4 mol/L at a temperature of not less than 70° C., and heated ethanol is added, then the mixture is cooled for precipitation of the crystals. Use of the hydrochloric acid having a concentration of not less than 4 mol/L for dissolution of the sapropterin hydrochloride is important for selective production of the α form crystal. When the hydrochloric acid used has a concentration of less than 4 mol/L, the β form crystals will be precipitated. The concentration of the hydrochloric acid is more preferably 4 to 12 mol/L, and most preferably 4 to 10 mol/L. Amount of the hydrochloric acid used is not particularly limited, and the hydrochloric acid is preferably used at 2.0 to 6.0-fold weight, and more preferably at 3.4-fold weight of the mass of the sapropterin hydrochloride.

Amount of the ethanol used is not particularly limited. However, the ethanol is preferably used at an amount of 2 to 10-fold volume, and more preferably at 2 to 7-fold volume of the total amount of the sapropterin hydrochloride and the hydrochloric acid (in volume) in view of improving the yield of the α form crystals.

The mixture of the sapropterin hydrochloride and the hydrochloric acid is dissolved by heating the mixture to a temperature of 70° C. or more. The components may be mixed in any order, and the components may be preliminary heated to a temperature of 70° C. or higher, or alternatively, the components may be mixed before heating the mixture to a temperature of 70° C. or higher. These two components dissolve completely when they are heated to a temperature of 70° C. or higher. The components or the mixture is preferably heated to a temperature of 70 to 85° C., more preferably to 70 to 80° C., and most preferably to 75 to 80° C.

Heated ethanol is subsequently added to the resulting sapropterin hydrochloride solution while the temperature is maintained by heating, and the mixture is cooled at a cooling rate of 3° C./min or less to a temperature of 40 to 55° C. to thereby precipitate the crystals. In such a case, α form crystals of sapropterin hydrochloride selectively precipitates. β form crystals will precipitate when the cooling rate is 8.0° C./min or higher. The cooling rate is more preferably 0.1 to 3° C./min, and more preferably 0.2 to 2.5° C./min.

With regard to a precipitation temperature, α form crystals is obtainable selectively when the crystals are precipitated at 40 to 55° C. while β form crystals precipitates when the precipitation is conducted at a temperature less than 40° C. Crystal precipitation at a temperature exceeding 55° C. will not be efficient.

When the crystals precipitated at 40 to 55° C. are filtered at the same range of temperature, highly pure α form crystals can be isolated. The α form crystals may be cooled after the isolation.

The resulting α form crystals of the sapropterin hydrochloride are highly stable under heat and humidity, and quite advantageous for a long term storage and in pharmaceutical preparation steps; therefore it is important in supplying high quality drug in a stable manner.

EXAMPLES

Next, the present invention is described in further detail by referring to Examples which by no means limit the scope of the present invention.

Example 1

To 9.10 g of 5.3 mol/L hydrochloric acid was added 2.70 g of sapropterin hydrochloride, and the mixture was stirred at an external temperature of 80° C. for dissolution (volume of the solution, 10 ml). When the internal temperature reached 75 to 80° C., 35 ml of heated ethanol (3.5-fold volume of the sapropterin hydrochloride solution) was added, and the mixture was cooled at a cooling rate of 1.2° C./min to an internal temperature of 55° C. Precipitated crystals were collected by filtration, washed with heated ethanol, and dried under reduced pressure at an external temperature of 40° C. Crystals of sapropterin hydrochloride were obtained at yield of 1.75 g and a recovery rate of 65%.

FIG. 1 shows infrared absorption spectrum, and FIG. 2 shows X ray diffraction spectrum of the resulting crystals. FIGS. 1 and 2 indicate that the resulting crystals were a form crystals.

Reference Example 1

To 9.10 g of 3.3 mol/L hydrochloric acid was added 2.70 g of sapropterin hydrochloride, and the mixture was stirred at an external temperature of 80° C. for dissolution (volume of the solution, 10 ml). When the internal temperature reached 75 to 80° C., 35 ml of hot ethanol (3.5-fold volume of the sapropterin hydrochloride solution) was added, and the mixture was cooled at a cooling rate of 0.2° C./min to an internal temperature of 55° C. Precipitated crystals were collected by filtration, washed with heated ethanol, and dried under reduced pressure at an external temperature of 40° C. Crystals of sapropterin hydrochloride were obtained at yield of 0.75 g and a recovery rate of 28%.

FIG. 3 shows infrared absorption spectrum, and FIG. 4 shows X ray diffraction spectrum of the resulting crystals. FIGS. 3 and 4 indicate that the resulting crystals were β form crystals.

Reference Example 2

To 9.10 g of 5.3 mol/L hydrochloric acid was added 2.70 g of sapropterin hydrochloride, and the mixture was stirred at an external temperature of 80° C. for dissolution (volume of the solution, 10 ml). When the internal temperature reached 75 to 80° C., 35 ml of heated ethanol (3.5-fold volume of the sapropterin hydrochloride solution) was added, and the mixture was cooled at a cooling rate of 0.4° C./min to an internal temperature of 20° C. Precipitated crystals were collected by filtration, washed with heated ethanol, and dried under reduced pressure at an external temperature of 40° C. Crystals of sapropterin hydrochloride were obtained at an yield of 2.15 g and a recovery rate of 80%. X ray spectrum of the resulting crystals was measured, and the results confirmed that the crystals were mixed crystals of α form and β form.

Test Example 1

Hydrochloric Acid Concentration

To 9.10 g each of hydrochloric acid at 3.3 mol/L, 4.0 mol/L, 4.6 mol/L, 5.3 mol/L or 10 mol/L was added 2.70 g of sapropterin hydrochloride, and the mixture was stirred at an external temperature of 80° C. for dissolution. Internal temperature was elevated to 75 to 80° C. To the solution was added 35 ml of hot ethanol, and the mixture was cooled at a cooling rate at 0.2 to 2.5° C./min to an inner temperature of 55° C. for precipitation. Crystals of sapropterin hydrochloride were then obtained at a recovery rate of 28 to 88%. X ray spectrum of the resulting crystals was measured, and the results confirmed that the crystals obtained in each condition were as shown in Table 1. α form crystal was obtained at 4.0 mol/L to 10 mol/L.

TABLE 1

| HCl concentration | Cooling rate | Crystal form | Recovery rate |
|---|---|---|---|
| 3.3 mol/L | 0.2° C./min | β | 28% |
| 4.0 mol/L | 0.7° C./min | α | 39% |
| 4.6 mol/L | 2.5° C./min | α | 51% |
| 5.3 mol/L | 1.2° C./min | α | 65% |
| 10 mol/L | 2.3° C./min | α | 88% |

Test Example 2

Temperature at Precipitation

To 9.10 g of 5.3 mol/L hydrochloric acid was added 2.70 g of sapropterin hydrochloride, and the mixture was stirred at an external temperature of 80° C. for dissolution. When the internal temperature reached 75 to 80° C., 35 ml of hot ethanol was added, and the mixture was cooled at a cooling rate of 1.0 to 1.2° C./min to an internal temperature of 20° C., 30° C., 40° C. or 55° C. Crystals of sapropterin hydrochloride were obtained at a recovery rate of 65 to 80%. X ray spectrum of the resulting crystals was measured, and the crystals produced in each condition were as shown in Table 2. α form crystals were obtained at a precipitation temperature of 40° C. to 55° C.

TABLE 2

| Temperature | Cooling rate | Crystal form | Recovery rate |
|---|---|---|---|
| 20° C. | 1.1° C./min | α + β | 80% |
| 30° C. | 1.0° C./min | α + β | 70% |
| 40° C. | 1.1° C./min | α | 69% |
| 55° C. | 1.2° C./min | α | 65% |

Test Example 3

Cooling Rate

To 9.10 g of 5.3 mol/L hydrochloric acid was added 2.70 g of sapropterin hydrochloride, and the mixture was stirred at an external temperature of 80° C. for dissolution. When the internal temperature reached 75 to 80° C., 35 ml of hot ethanol was added, and the mixture was cooled to an internal temperature of 55° C. in 3 minutes (about 8° C./min), in 21 minutes (about 1.2° C./min), or 2 hours and 10 minutes (about 0.2° C./min) to produce sapropterin hydrochloride. Crystals of sapropterin hydrochloride were obtained at a recovery rate of 53 to 65%. X ray spectrum of the resulting crystals was measured, and the crystals produced in each condition were as shown in Table 3. α form crystals were obtained at a cooling rate of 1.2° C./min or slower than this rate.

TABLE 3

| Cooling rate | Crystal form | Recovery rate |
|---|---|---|
| about 8.0° C./min | α + β | 53% |
| about 1.2° C./min | α | 65% |
| about 0.2° C./min | α | 63% |

Test Example 4

Amount of Ethanol Used

To 9.10 g of 5.3 mol/L hydrochloric acid was added 2.70 g of sapropterin hydrochloride, and the mixture was stirred at an external temperature of 80° C. for dissolution (solution volume, 10 mL). When the internal temperature reached 75 to 80° C., heated ethanol at an amount varied in the range of 20 mL to 70 mL (2 to 7-fold volume of the sapropterin hydrochloride solution) was added, and the mixture was cooled at a cooling rate of 0.8 to 1.3° C./min to an internal temperature of 55° C. α form crystals of sapropterin hydrochloride were obtained at a recovery rate of 39 to 80% as shown in Table 4. Amount of the ethanol used had no relation with the crystal form of the precipitated crystals.

TABLE 4

| Ethanol | Amount of ethanol in relation to sapropterin hydrochloride solution | Cooling rate | Crystal form | Recovery rate |
|---|---|---|---|---|
| 20 mL | 2-fold volume | 1.3° C./min | α | 39% |
| 35 mL | 3.5-fold volume | 1.2° C./min | α | 65% |
| 70 mL | 7-fold volume | 0.8° C./min | α | 80% |

The invention claimed is:

1. A method for producing α form crystal of sapropterin hydrochloride comprising the steps of dissolving sapropterin hydrochloride with hydrochloric acid at a concentration of not less than 4 mol/L at not less than 70° C.; adding heated ethanol to the solution; and cooling the solution at a cooling rate of not faster than 3° C./min to a temperature of 40 to 55° C. to precipitate the crystals.

2. The production method according to claim 1 wherein the sapropterin hydrochloride is dissolved at a temperature in the range of 75 to 80° C.

3. The production method according to claim 1 or 2 wherein the ethanol is used at an amount of 2 to 10-fold volume in relation to the solution of sapropterin hydrochloride in hydrochloric acid.

4. The production method according to claim 1 wherein the cooling rate is in the range of 0.1 to 3° C./min.

* * * * *